(12) United States Patent
Biel et al.

(10) Patent No.: US 11,058,151 B2
(45) Date of Patent: Jul. 13, 2021

(54) REFILL ADAPTER CAP FOR A REFILL RECEPTACLE TO REFILL LIQUID IN AN ELECTRONIC SMOKING DEVICE

(71) Applicant: Fontem Holdings 1 B.V., Amsterdam (NL)

(72) Inventors: Stefan Biel, Hamburg (DE); Andreas Beer, Grasbrunn (DE)

(73) Assignee: Fontem Holdings 1 B.V., Amsterdam (NL)

(*) Notice: Subject to any disclaimer, the term of this patent is extended or adjusted under 35 U.S.C. 154(b) by 310 days.

(21) Appl. No.: 16/330,331

(22) PCT Filed: Sep. 6, 2017

(86) PCT No.: PCT/EP2017/072340
§ 371 (c)(1),
(2) Date: Mar. 4, 2019

(87) PCT Pub. No.: WO2018/046539
PCT Pub. Date: Mar. 15, 2018

(65) Prior Publication Data
US 2019/0223506 A1 Jul. 25, 2019

(30) Foreign Application Priority Data

Sep. 6, 2016 (EP) .................................. 16187476
Sep. 14, 2016 (EP) .................................. 16188825

(51) Int. Cl.
*A24F 15/015* (2020.01)
*B67B 7/00* (2006.01)
(Continued)

(52) U.S. Cl.
CPC ............... *A24F 15/015* (2020.01); *B67B 7/26* (2013.01); *A24F 40/00* (2020.01); *A24F 40/10* (2020.01); *A61M 2209/045* (2013.01)

(58) Field of Classification Search
CPC ....................................................... A24F 15/015
See application file for complete search history.

(56) References Cited

U.S. PATENT DOCUMENTS 9,497,993 B2 * 11/2016 Vallar .................... A24B 15/00
10,440,991 B2 * 10/2019 Levitz ................... F16K 15/183
(Continued)

FOREIGN PATENT DOCUMENTS

CN   201379073 Y   1/2010
CN   102379458 A   3/2012
(Continued)

*Primary Examiner* — James Harvey
(74) *Attorney, Agent, or Firm* — Dykema Gossett PLLC

(57) ABSTRACT

A refill adapter cap (100) is provided for a refill receptacle adapted to refill the liquid reservoir of an electronic smoking device via the refill adapter cap, wherein the refill adapter cap comprises a first end (101) with an opening (110) and a connection portion (120), adapted for the connection to a refill receptacle. Furthermore, the refill adapter cap comprises a second end (102) with an injection portion (130) that protrudes from the second end and defines a liquid outlet hole (131). Moreover, the refill adapter cap comprises a liquid flow channel (140) interconnecting the first end and the second end, allowing for liquid to flow through the refill adapter cap. The liquid flow channel comprises a slope section (160) adapted to reduce the flow rate of liquid passing the liquid flow channel.

20 Claims, 9 Drawing Sheets

(51) Int. Cl.
*A24F 40/00* (2020.01)
*A24F 40/10* (2020.01)

(56) References Cited

U.S. PATENT DOCUMENTS

| | | | |
|---|---|---|---|
| 10,865,095 B2* | 12/2020 | Scott | ............... B65D 47/06 |
| 2002/0179635 A1 | 12/2002 | Incardona et al. | |
| 2012/0167906 A1 | 7/2012 | Gysland | |
| 2014/0076310 A1 | 3/2014 | Newton | |
| 2014/0283946 A1 | 9/2014 | Kribs | |
| 2019/0223506 A1* | 7/2019 | Biel | ............... A24F 47/008 |

FOREIGN PATENT DOCUMENTS

| | | |
|---|---|---|
| CN | 203934663 U | 11/2014 |
| WO | 2016/096337 A1 | 6/2016 |

\* cited by examiner

REFILL ADAPTER CAP FOR A REFILL RECEPTACLE TO REFILL LIQUID IN AN ELECTRONIC SMOKING DEVICE

CROSS-REFERENCE TO RELATED APPLICATIONS

This application is a national stage filing based upon international application no. PCT/EP2017/072340, filed 6 Sep. 2017 and published in English on 15 Mar. 2018 under international publication no. WO 2018/046539 (the '539 application). This application also claims priority to European patent application no. EP 16187476.3 (the '476 application), filed 6 Sep. 2016 and European patent application no. EP 16188825.0 (the '825 application), filed 14 Sep. 2016. The '539, '476, and '825 applications are all hereby incorporated by reference as though fully set forth herein.

The present invention relates generally to electronic smoking devices and in particular electronic cigarettes.

BACKGROUND OF THE INVENTION

An electronic smoking device, such as an electronic cigarette (e-cigarette), typically has a housing accommodating an electric power source (e.g. a single use or rechargeable battery, electrical plug, or other power source), and an electrically operable atomizer. The atomizer vaporizes or atomizes liquid supplied from a reservoir and provides vaporized or atomized liquid as an aerosol. Control electronics control the activation of the atomizer. In some electronic cigarettes, an airflow sensor is provided within the electronic smoking device, which detects a user puffing on the device (e.g., by sensing an under-pressure or an air flow pattern through the device). The airflow sensor indicates or signals the puff to the control electronics to power up the device and generate vapor. In other e-cigarettes, a switch is used to power up the e-cigarette to generate a puff of vapor.

Most electronic smoking devices are configured to be refilled when the liquid reservoir of the electronic smoking device is emptied. Often, a procedure for the refill of the liquid reservoir of an electronic smoking device comprises a disassembling of the electronic smoking device in order to expose a refill opening of the liquid reservoir of the electronic smoking device. In most cases, a refill bottle is used to refill the liquid reservoir, wherein the refill bottles of the state of the art mostly comprise a simple pipette like attachment or cap which shall allow for liquid to be transported from the refill bottle into the liquid reservoir via the refill opening.

However, such refill bottles with attachments or caps like the aforementioned often cause the liquid to spill during the refill procedure which can be perceived as highly inconvenient for the user of the electronic smoking device. Furthermore, when refilling the liquid reservoir, it is necessary to avoid dripping liquid into the air tube. Liquid that passes down the air tube into the atomizer may flood the atomizer and temporarily stops the device from working. When the device is then operated to clear the misplaced liquid, this often results in leakage as the misplaced liquid finds its way out of the atomizer through the air passage. Clearing the air passage is also often accompanied by a "gurgling" sound and sensation which users find unpleasant. Moreover, difficulties in refilling an electronic smoking device may cause users to miss the reservoir causing their fingers holding the electronic smoking device to come into contact with the liquid for atomization. Further liquid may spill from the reservoir prior to the mouthpiece of the device being reattached closing the open end of the reservoir. Often liquid for atomization is relatively greasy and is impregnated with flavors which makes coming into contact unpleasant and undesirable as the liquid needs to be washed off and odors from the liquid may be retained on the hands. Furthermore, there is a risk that users may accidentally ingest the liquid if the liquid is not washed off.

SUMMARY OF THE INVENTION

In accordance with one aspect of the present invention there is provided a refill adapter cap for a refill receptacle adapted to refill the liquid reservoir of an electronic smoking device via the refill adapter cap, wherein the refill adapter cap comprises a first end with an opening and a connection portion, adapted for the connection to a refill receptacle. Furthermore, the refill adapter cap comprises a second end with an injection portion that protrudes from the second end and comprises a liquid outlet hole. Moreover, the refill adapter cap comprises a liquid flow channel interconnecting the first end and the second end, allowing for liquid to flow through the refill adapter cap. The liquid flow channel comprises a slope section adapted to reduce the flow rate of liquid passing the liquid flow channel.

The characteristics, features and advantages of this invention and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, same element numbers indicate same elements in each of the views.

DESCRIPTION OF THE PREFERRED EMBODIMENTS

Figure 1:
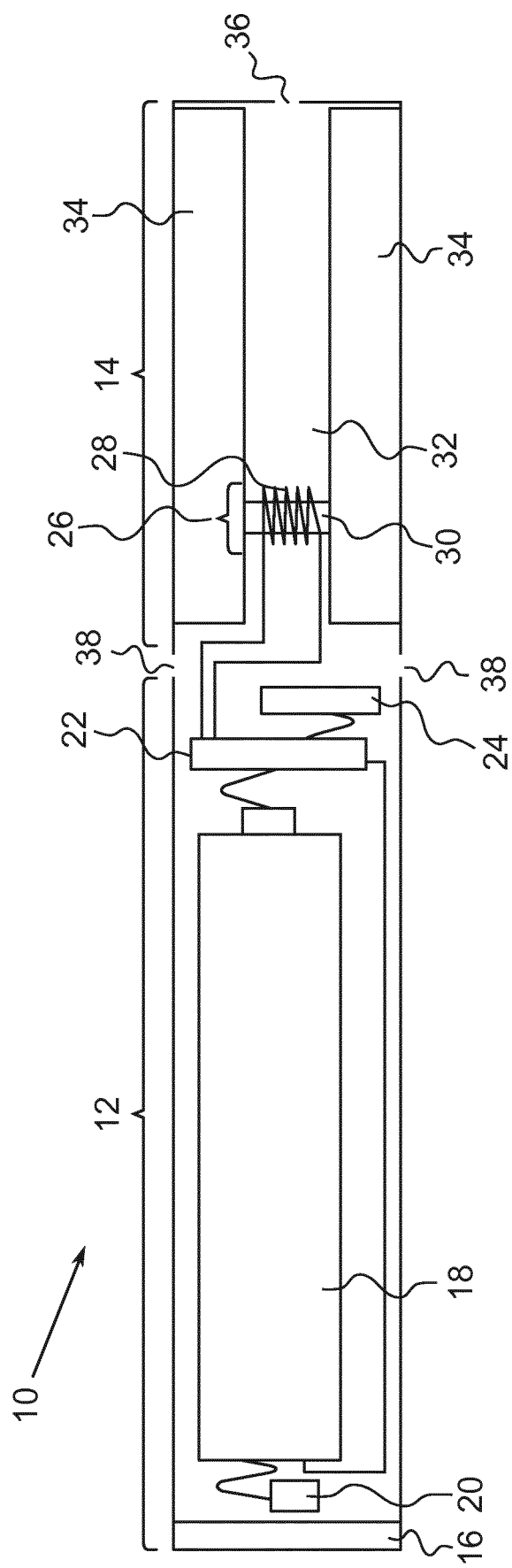
FIG. 1 is a schematic cross-sectional illustration of an exemplary e-cigarette.

Throughout the following, an electronic smoking device will be exemplarily described with reference to an e-cigarette. As is shown in FIG. 1, an e-cigarette 10 typically has a housing comprising a cylindrical hollow tube having an end cap 16. The cylindrical hollow tube may be a single-piece or a multiple-piece tube. In FIG. 1, the cylindrical hollow tube is shown as a two-piece structure having a power supply portion 12 and an atomizer/liquid reservoir portion 14. Together the power supply portion 12 and the atomizer/liquid reservoir portion 14 form a cylindrical tube which can be approximately the same size and shape as a conventional cigarette, typically about 100 mm with a 7.5 mm diameter, although lengths may range from 70 to 150 or 180 mm, and diameters from 5 to 28 mm.

The power supply portion 12 and atomizer/liquid reservoir portion 14 are typically made of metal, e.g. steel or aluminum, or of hardwearing plastic and act together with the end cap 16 to provide a housing to contain the components of the e-cigarette 10. The power supply portion 12 and an atomizer/liquid reservoir portion 14 may be configured to fit together by a friction push-fit, a snap-fit, or a bayonet attachment, magnetic fit, or screw threads. The end cap 16 is provided at the front end of the power supply portion 12. The end cap 16 may be made from translucent plastic or other translucent material to allow a light-emitting diode (LED) 20 positioned near the end cap to emit light through the end cap. The end cap can be made of metal or other materials that do not allow light to pass.

An air inlet may be provided in the end cap, at the edge of the inlet next to the cylindrical hollow tube, anywhere along the length of the cylindrical hollow tube, or at the connection of the power supply portion 12 and the atomizer/liquid reservoir portion 14. FIG. 1 shows a pair of air inlets 38 provided at the intersection between the power supply portion 12 and the atomizer/liquid reservoir portion 14.

A power supply, preferably a battery 18, an LED 20, control electronics 22 and optionally an airflow sensor 24 are provided within the cylindrical hollow tube power supply portion 12. The battery 18 is electrically connected to the control electronics 22, which are electrically connected to the LED 20 and the airflow sensor 24. In this example, the LED 20 is at the front end of the power supply portion 12, adjacent to the end cap 16 and the control electronics 22 and airflow sensor 24 are provided in the central cavity at the other end of the battery 18 adjacent to the atomizer/liquid reservoir portion 14.

The airflow sensor 24 acts as a puff detector, detecting a user puffing or sucking on the atomizer/liquid reservoir portion 14 of the e-cigarette 10. The airflow sensor 24 can be any suitable sensor for detecting changes in airflow or air pressure, such as a microphone switch including a deformable membrane which is caused to move by variations in air pressure. Alternatively, the sensor may be a Hall element or an electro-mechanical sensor.

The control electronics 22 are also connected to an atomizer 26. In the example shown, the atomizer 26 includes a heating coil 28 which is wrapped around a wick 30 extending across a central passage 32 of the atomizer/liquid reservoir portion 14. The coil 28 may be positioned anywhere in the atomizer 26 and may be transverse or parallel to the liquid reservoir 34. The wick 30 and heating coil 28 do not completely block the central passage 32. Rather an air gap is provided on either side of the heating coil 28 enabling air to flow past the heating coil 28 and the wick 30. The atomizer may alternatively use other forms of heating elements, such as ceramic heaters, or fiber or mesh material heaters. Nonresistance heating elements such as sonic, piezo and jet spray may also be used in the atomizer in place of the heating coil.

The central passage 32 is surrounded by a cylindrical liquid reservoir 34 with the ends of the wick 30 abutting or extending into the liquid reservoir 34. The wick 30 may be a porous material such as a bundle of fiberglass fibers, with liquid in the liquid reservoir 34 drawn by capillary action from the ends of the wick 30 towards the central portion of the wick 30 encircled by the heating coil 28.

The liquid reservoir 34 may alternatively include wadding soaked in liquid which encircles the central passage 32 with the ends of the wick 30 abutting the wadding. In other embodiments, the liquid reservoir 34 may comprise a toroidal cavity arranged to be filled with liquid and with the ends of the wick 30 extending into the toroidal cavity. In further embodiments, the liquid reservoir 34 may have the shape of a plain cylinder or the shape of a tube. Furthermore, the liquid reservoir 34 may be arranged such that an opening or an adapter counterpart (not shown in FIG. 1) for a refill adapter or a refill adapter cap is exposed when a portion of the e-cigarette 10, e.g. the atomizer/liquid reservoir portion 14 itself is detached from the e-cigarette 10.

An air inhalation port 36 is provided at the back end of the atomizer/liquid reservoir portion 14 remote from the end cap 16. The inhalation port 36 may be formed from the cylindrical hollow tube atomizer/liquid reservoir portion 14 or maybe formed in an end cap.

In use, a user sucks on the e-cigarette 10. This causes air to be drawn into the e-cigarette 10 via one or more air inlets, such as air inlets 38, and to be drawn through the central passage 32 towards the air inhalation port 36. The change in air pressure which arises is detected by the airflow sensor 24, which generates an electrical signal that is passed to the control electronics 22. In response to the signal, the control electronics 22 activate the heating coil 28, which causes liquid present in the wick 30 to be vaporized creating an aerosol (which may comprise gaseous and liquid components) within the central passage 32. As the user continues to suck on the e-cigarette 10, this aerosol is drawn through the central passage 32 and inhaled by the user. At the same time, the control electronics 22 also activate the LED 20 causing the LED 20 to light up which is visible via the translucent end cap 16 mimicking the appearance of a glowing ember at the end of a conventional cigarette. As liquid present in the wick 30 is converted into an aerosol, more liquid is drawn into the wick 30 from the liquid reservoir 34 by capillary action and thus is available to be converted into an aerosol through subsequent activation of the heating coil 28.

Some e-cigarettes are intended to be disposable and the electric power in the battery 18 is intended to be sufficient to vaporize the liquid contained within the liquid reservoir 34, after which the e-cigarette 10 is thrown away. In other embodiments the battery 18 is rechargeable and the liquid reservoir 34 is refillable. In the cases where the liquid reservoir 34 is a toroidal cavity, this may be achieved by refilling the liquid reservoir 34 via a refill port or a refill adapter counterpart. In other embodiments the atomizer/liquid reservoir portion 14 of the e-cigarette 10 is detachable from the power supply portion 12 and a new atomizer/liquid reservoir portion 14 can be fitted with a new liquid reservoir 34 thereby replenishing the supply of liquid. In some cases, replacing the liquid reservoir 34 may involve replacement of the heating coil 28 and the wick 30 along with the replacement of the liquid reservoir 34. A replaceable unit comprising the atomizer 26 and the liquid reservoir 34 is called a cartomizer.

The new liquid reservoir 34 may be in the form of a cartridge having a central passage 32 through which a user inhales aerosol. In other embodiments, aerosol may flow around the exterior of the cartridge 32 to an air inhalation port 36.

Of course, in addition to the above description of the structure and function of a typical e-cigarette 10, variations also exist. For example, the LED 20 may be omitted. The airflow sensor 24 may be placed adjacent to the end cap 16 rather than in the middle of the e-cigarette. The airflow sensor 24 may be replaced with a switch which enables a user to activate the e-cigarette manually rather than in response to the detection of a change in air flow or air pressure.

Different types of atomizers may be used. Thus, for example, the atomizer may have a heating coil in a cavity in the interior of a porous body soaked in liquid. In this design aerosol is generated by evaporating the liquid within the porous body either by activation of the coil heating the porous body or alternatively by the heated air passing over or through the porous body. Alternatively, the atomizer may use a piezoelectric atomizer to create an aerosol either in combination or in the absence of a heater.

Figure 2:
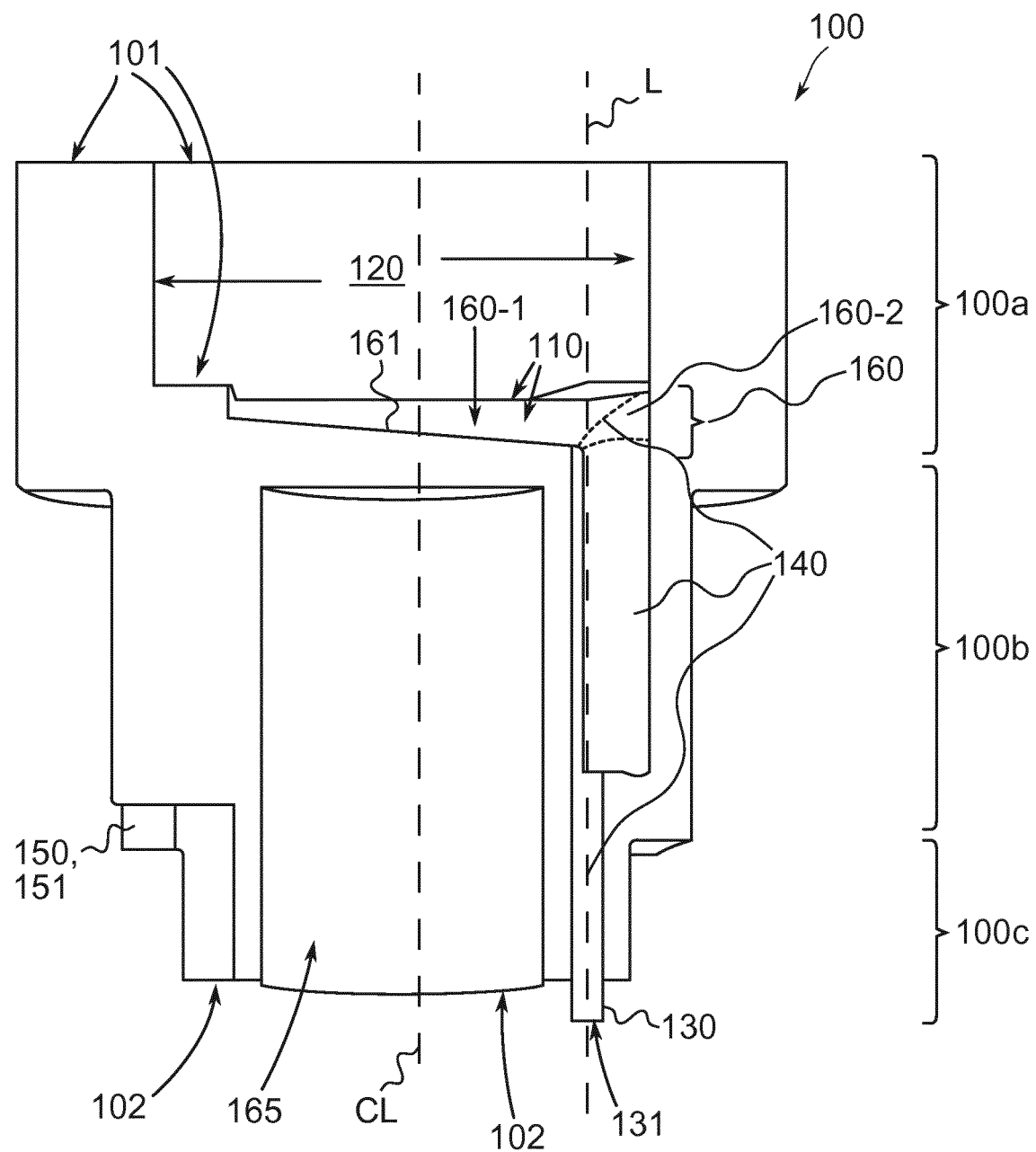
FIG. 2 is a schematic cross-sectional illustration of a first embodiment of a refill adapter cap for a refill receptacle.

FIG. 2 is a schematic cross-sectional illustration of a first embodiment of a refill adapter cap 100 for a refill receptacle (not shown). In this embodiment, the refill adapter cap 100 is an adapter cap 100 for a refill receptacle that is adapted to refill the liquid reservoir of an electronic smoking device via the refill adapter cap 100. In this embodiment, the refill receptacle exemplarily is a refill bottle (not shown) that can comprise or be made of glass, plastic or the like and which resembles an eye-drop bottle or a bottle for medical products. In this embodiment, the refill adapter cap 100 can be used with a refill bottle that is suited to refill the liquid reservoir 34 of the electronic smoking device 10 described hereinbefore. The refill adapter cap 100 comprises a first end 101 with an opening 110 and a connection portion 120, adapted for the connection to a refill receptacle. Furthermore, the refill adapter cap 100 comprises a second end 102 with an injection portion 130 that protrudes from the second end 102 and comprises a liquid outlet hole 131. The second end 102 is an end of the refill adapter cap 100 that differs from the first end 102. Moreover, the refill adapter cap 100 comprises a liquid flow channel 140 that interconnects the first end 101 and the second end 102, allowing for liquid to flow through the refill adapter cap 100. Furthermore, in the embodiment shown in FIG. 2, the refill adapter cap 100 comprises one air release portion 150 that is realized as a notch 151. However, also other embodiments of refill adapter caps 100 can be realized, comprising more than one air release portion 150 or one or multiple air release holes. The liquid flow channel 140 comprises a slope section 160 adapted to reduce the flow rate of liquid passing the liquid flow channel 140. With such a refill adapter cap 100, it is provided an adapter cap 100 that allows for an easy, safe and especially spill-free refilling of the liquid reservoir of an electronic smoking device. In use with a refill bottle containing liquid to be atomized, the slope section 160 of the liquid flow channel 140 causes the liquid flowing within the liquid flow channel 140 to be slowed down to a predefined rate. Via the injection portion 130, the slowed down liquid flows precisely into a corresponding opening (not shown) when the refill adapter cap 100 is in a connected state.

In this embodiment, the refill adapter cap 100 comprises a first, a second and a third circular section 100a, 100b, 100c that substantially have the shape of cylinders. These sections 100a, 100b, 100c differ from one another in their respective diameter and together form the refill adapter cap 100. The outer sides and edges of the first section/the first cylinder 100a define the first end 101 of the refill adapter cap 100. The first section 100a or the first cylinder is the cylinder of the refill adapter cap 100 that comprises the greatest diameter, wherein the first section 100a comprises the connection portion 120 that in this embodiment exemplarily comprises a screw-fit connection. An advantage of that may be that the refill adapter cap 100 can easily be connected to a refill receptacle 200 as for example a refill bottle.

In this embodiment, the screw-fit connection element is realized as a female thread. An advantage of that may be that the refill adapter cap 100 can easily be screwed onto a refill bottle via the female thread. The drill hole forming the receiving section of the connection portion 120 with the internal female thread arranged on the inner sides of the drill hole opens out into the opening 110 of the first end 101. The opening 110 represents the entrance of the liquid flow channel 140 that interconnects the first end 101 with the second end 102 of the refill adapter cap 100. The liquid flow channel 140 comprises a slope section 160 that extends from the first end 101 along a part of the liquid flow channel 140 and has a tapering cross-section. An advantage of that may be that liquid that enters the refill adapter cap 100 and the opening 110 from a refill receptacle 200 or—as in this case—a refill bottle, is slowed down to a predefined flow rate so that spilling of liquid is avoided when the liquid exits the liquid flow channel 140 via the injection portion 130. In more detail, the slope section 160 extends from the opening 110 of the liquid flow channel 140 down to an area of a lower end of the first section 100a where it transitions into a lower part of the liquid flow channel 140. Therefore, at the first end 101, the slope section 160 has a diameter that is equal to the diameter of the opening 110. Expressed in other words, the slope section 160 of the liquid flow channel 140 at the first end 101 has a diameter that is as great as the diameter of the opening 110. An advantage of that may be that liquid entering the refill adapter cap 100 can immediately enter the slope section 160 which does not interrupt the flow of liquid. Furthermore, such an embodiment allows for an eased manufacturing of the refill adapter cap 100. In this first embodiment, the slope section 160 of the liquid flow channel 140 has the shape of a funnel. An advantage of that may be that such a funnel design easily allows for an efficient decrease of the flow rate of liquid entering the slope section 160. In this embodiment, the funnel comprises an accumulative portion 160-1 for the reception of liquid entering the slope section 160 via the opening 110 and a discharge portion 160-2 for the transport of liquid from the funnel to the lower part of the liquid flow channel 140.

The discharge portion 160-2 of the funnel is not arranged centrally under the accumulative portion 160-1 but displaced on a side of the funnel, aligned with the lower part of the liquid flow channel 140.

The slope section 160 narrows along a direction pointing from the first end 101 to the second end 102 of the refill adapter cap 100. Moreover, the slope section 160 comprises a slanted surface 161 guiding liquid which enters the refill adapter cap 100 via the opening 110 into a lower part of the liquid flow channel 140. The lower part of the liquid flow channel 140 extends along a line L that is displaced in parallel with respect to a centerline CL of the refill adapter cap 100. An advantage of that may be that a central part of the refill adapter cap 100 can be provided with a center hole 165 allowing for the refill adapter cap 100 to be centered for example around a protrusion-part of an electronic smoking device, adapted for the positioning adjustment of the refill adapter cap 100. Expressed in other words, the slanted surface 161 of the slope section 160 flows into a lower part of the liquid flow channel 140 that extends along a side portion of the refill adapter cap 100, the side portion representing a rim of the refill adapter cap 100, surrounding the center hole 165.

The liquid flow channel 140 extends along the second and the third circular section 100b, 100c that also substantially have the shape of cylinders. However, the diameter of the second circular section 100*b* is smaller than the diameter of the first circular section 100*a* and the diameter of the third circular section 100*c* is smaller than the diameter of the second circular section 100*b*. In this embodiment, the lower part of the liquid flow channel 140 substantially extends through the second circular section 100*b* and has a diameter that is greater than the diameter of the lowest part of the liquid flow channel 140 substantially extending through the third circular section 100*c*. The diameter of the lowest part of the liquid flow channel 140 that is substantially extending through the third circular portion 100*c* is equal to the diameter of the injection portion 130 and to the diameter of the liquid outlet hole 131 respectively.

In this embodiment, the refill adapter cap 100 comprises an air release portion 150 on a side of the refill adapter cap 100. The air release portion 150 allows for a pressure equalization when the refill adapter cap 100 is connected to an electronic smoking device and when liquid is filled into a liquid reservoir of the electronic smoking device via the refill adapter cap 100, which will be further described in relation to FIG. 3.

Figure 3:
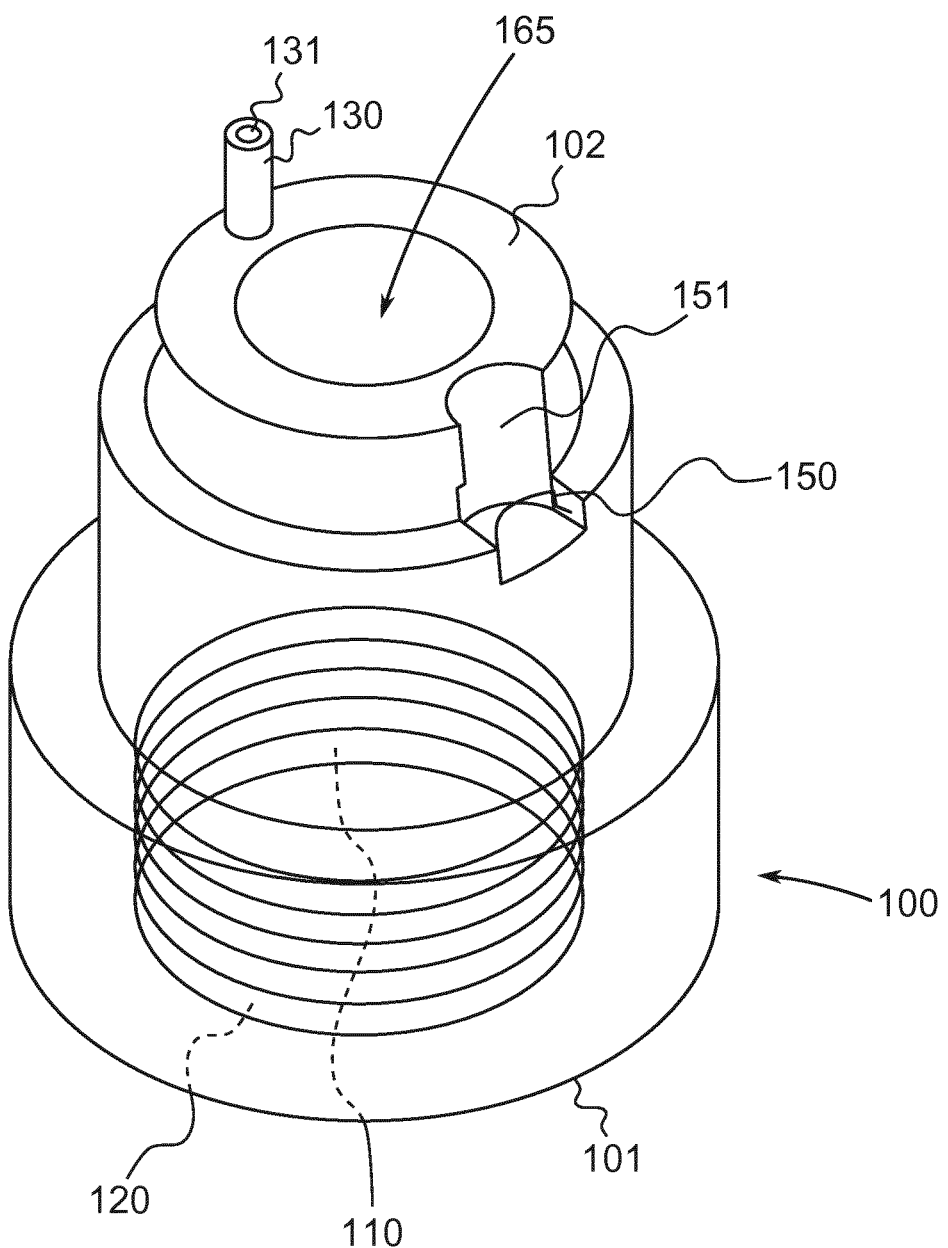
FIG. 3 is a schematic side view of the first embodiment of the refill adapter cap.

In FIG. 3, a schematic side view of the first embodiment of a refill adapter cap 100 is shown. In this figure, the refill adapter cap 100 is turned on the first end 101 so that the second end 102 with the center hole 165, the injection portion 130 with the liquid outlet hole 131 and the air release portion 150 can be seen. In this embodiment, the air release portion 150 is exemplarily realized as a notch 151 that is cut out of the side portion representing a rim surrounding the center hole 165. The notch 151 will prevent an opening within the electronic smoking device to be fully sealed by the second end 102 when the liquid refill cap 100 is inserted into the opening of the electronic smoking device. Therefore, air that is ousted out of the liquid reservoir of an electronic smoking device when the same is (re)filled with liquid can escape via the air release portion 150, so the notch 151 within the second end 102 of the refill adapter cap 100.

Furthermore, the screw-fit connection element of the connection portion 120 which in this embodiment is exemplarily realized as a female screw is indicated in FIG. 3 via circles which shall represent the internal thread of the connection portion 120. However, also other embodiments of refill adapter caps can be realized comprising other connection portions with other connection elements, for example with friction push-fit connection elements, snap-fit connection elements, bayonet attachment elements and/or magnetic fit connection elements. Furthermore, also other refill adapter caps comprising other connection portions can be realized, for example refill adapter caps that comprise a male thread or any other engagement element for the releasable connection of the refill adapter cap to a refill receptacle.

Figure 4:
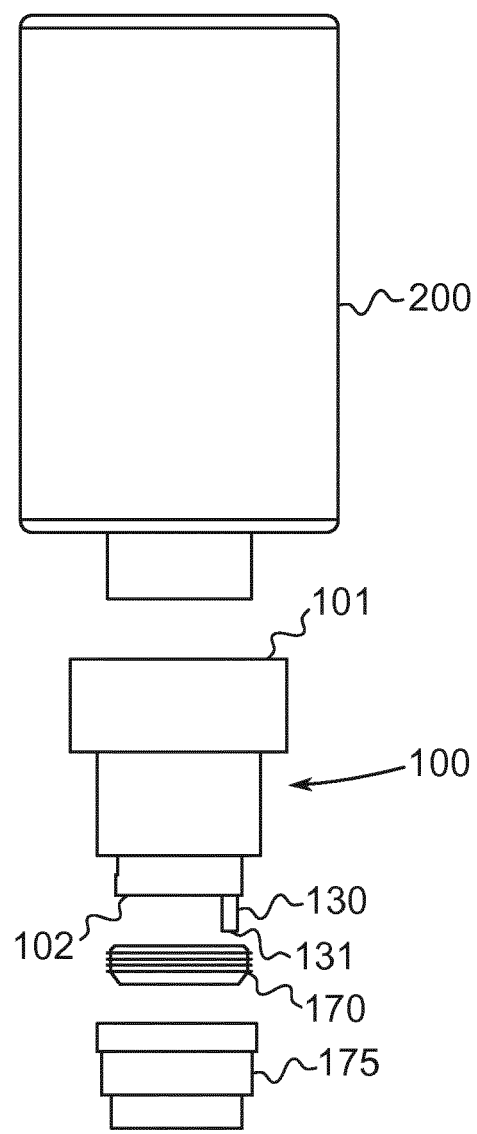
FIG. 4 is an exploded view of a second embodiment of a refill adapter cap for a refill receptacle.

In FIG. 4, an exploded view of a second embodiment of a refill adapter cap 100 for a refill receptacle 200 is shown. In more detail, FIG. 4 shows a refill receptacle 200 which is realized as a refill bottle and which comprises an e-liquid, so a liquid which is adapted to be vaporized or atomized by the atomizer of an electronic smoking device (not shown). Furthermore, FIG. 4 shows the refill adapter cap 100 as described hereinbefore from a side.

In this second embodiment, the refill adapter cap 100 further comprises an inlay cap 170 adapted to be arranged within an opening of an electronic smoking device, wherein the inlay cap 170 comprises an insertion hole (not shown in FIG. 4) for the reception of the injection portion 130 of the refill adapter cap 100, allowing for liquid to flow through the inlay cap 170. An advantage of that may be that the refill adapter cap 100 can simply be connected to the electronic smoking device comprising the liquid reservoir that needs to be refilled via the inlay cap 170. This allows for liquid to flow from the refill receptacle 200 through the refill adapter cap 100 and through the inlay cap 170 into the liquid reservoir. Therefore, the refill adapter cap 100 itself does not need to be provided with an own connection portion for the connection to an electronic smoking device and further can be used for a refill of different electronic smoking devices, as only the inlay cap 170 needs to be adjusted or chosen accordingly.

In FIG. 4, only a part of the atomizer/liquid reservoir portion of an electronic smoking device is shown which represents an adapter counterpart 175. The adapter counterpart 175 in this embodiment is arranged in front of the liquid reservoir (not shown) of the electronic smoking device. The inlay cap 170 comprises an outer screw which is adapted to engage with an internal thread (not shown) of the adapter counterpart 175.

Figure 5:
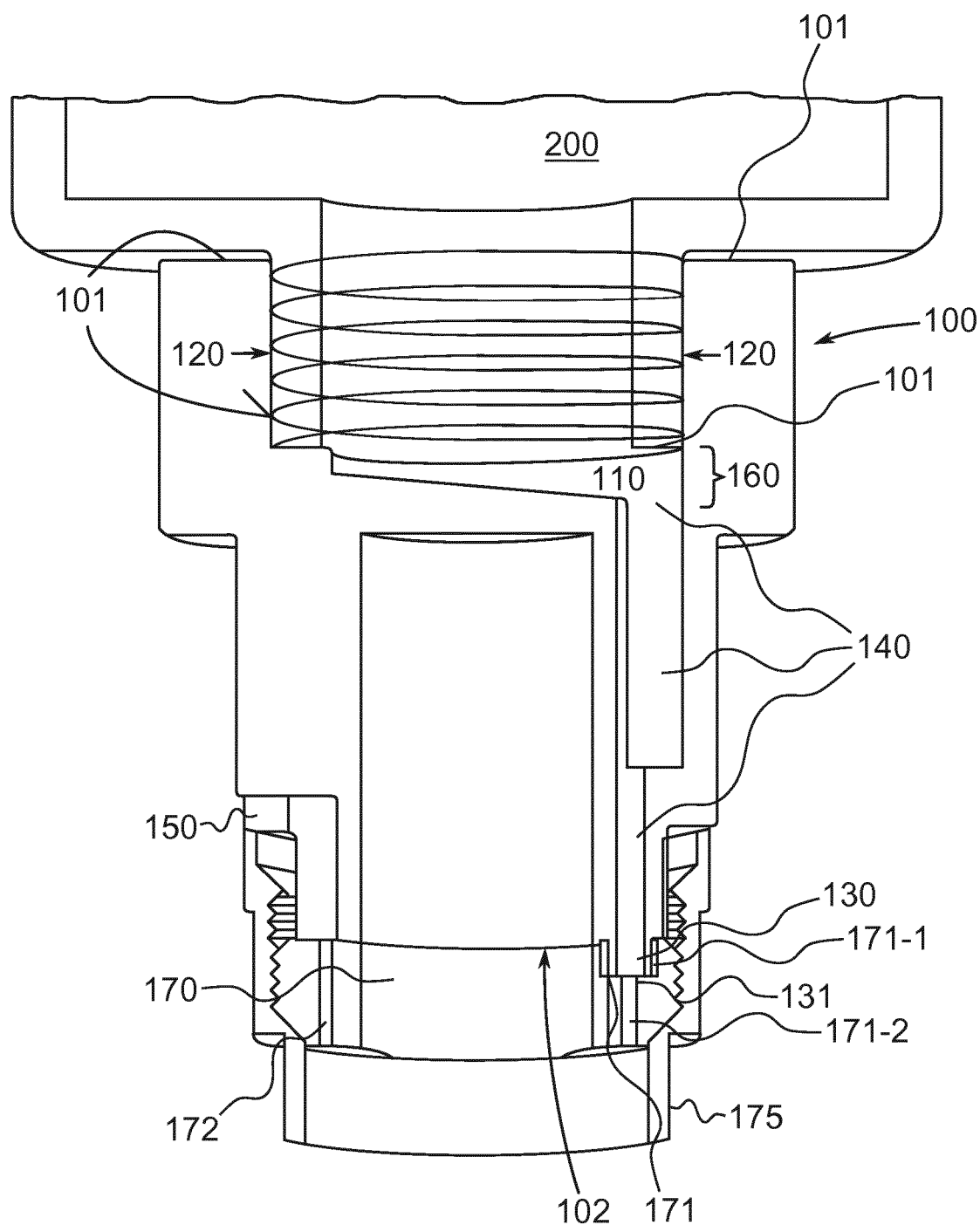
FIG. 5 is a schematic cross-sectional illustration of the second embodiment of a refill adapter cap in a connected state.

In FIG. 5, a schematic cross-sectional illustration of the second embodiment of a refill adapter cap 100 in a connected state is shown. In more detail, FIG. 5 shows a refill bottle with the second embodiment of a refill adapter cap 100 screwed thereon. The refill adapter cap 100 comprises a connection portion 120 with an internal screw thread that is screwed onto a corresponding external screw thread of a refill outlet portion of the refill receptacle 200 that in this embodiment is realized as a refill bottle. In a connected state, the opening 110 of the first end 101 of the refill adapter cap 100 is directly arranged on the opening of the refill bottle so that liquid exiting the refill bottle directly enters the opening 110 of the first end 110 and therefore the slope section 160 of the refill adapter cap 100. In a connected state, the upper outermost parts of the first end 101 of the refill adapter cap 100 are in contact with a bearing surface of the refill bottle.

Furthermore, the refill adapter cap 100 is inserted into an inlay cap 170 which is the inlay cap 170 described hereinbefore. Therefore, also in FIG. 5, the inlay cap 170 comprises an insertion hole 171 for the reception of the injection portion 130 of the refill adapter cap 100, allowing for liquid to flow through the refill adapter cap 100 and the inlay cap 170. The insertion hole 171 in this embodiment exemplarily resembles a channel through the inlay cap 170, the channel having two different parts 171-1, 171-2 with different diameters respectively. The diameter of the first part 171-1 of the insertion hole/channel 171 in the inlay cap 170 is chosen such that the injection portion 130 can be directly and fully inserted into the insertion hole 171 to an extent that is predefined by a connection state in that the second end 102 and the tip of the injection portion 130 of the refill adapter cap 100 are in direct contact with the surface of the inlay cap 170 respectively. The second part 171-2 of the insertion hole/channel 171 within the inlay cap 170 has a second, smaller diameter than the first part 171-1 of the insertion hole/channel 171. In the connected state of the refill adapter cap 100 shown in FIG. 5, the second part 171-2 of the insertion hole/channel 171 within the inlay cap 170 is aligned with the liquid outlet hole 131 of the injection portion 130. Moreover, the inlay cap 170 further comprises an airflow channel 172 allowing for air to flow through the inlay cap 170. An advantage of that may be that air that is ousted out of the liquid reservoir of an electronic smoking device, when the same is (re)filled with liquid, can escape via the airflow channel 172 in a fully connected state of the refill adapter cap 100. Furthermore, in a connected state of the refill adapter cap 100 and the inlay cap 170, the air release portion 150 is aligned with the air flow channel 172 of the inlay cap 170. Therefore, air that exits the airflow channel 172 is not pushed against the outermost surface of the second end 102 of the refill adapter cap 100 but is released via the air release portion 150. Therefore, a pressure equalization is always guaranteed.

In this second embodiment, the inlay cap 170 of the refill adapter cap 100 comprises an outer screw thread that can be threaded/screwed into a corresponding internal thread of an adapter counterpart 175 of an electronic smoking device. This adapter counterpart 175 in this second embodiment exemplarily is arranged within a cylindrical tube (not shown) forming the body of an electronic smoking device, wherein the opening of the adapter counterpart 175 is oriented perpendicular to the walls of the cylindrical tube when the adapter counterpart 175 is arranged within the tube. However, also other refill adapter caps 100 can be realized without or with other inlay caps 170 which are adapted to be connected with other adapter counterparts 175. Such refill adapter caps for example can comprise inlay caps 170 which are press-fitted or screw-fitted into a corresponding adapter counterpart.

When, as shown in FIG. 5, the refill adapter cap 100 is in a state connected to the electronic smoking device and to the refill bottle, liquid flows from the refill bottle into the opening 110 and thereby into the slope section 160 of the refill adapter cap 100. From the slope section 160, the liquid flows into the lower part of the liquid flow channel 140 from where it enters the injection portion 130 of the second end 102 of the refill adapter cap 100. The liquid then exits the refill adapter cap 100 via the liquid outlet hole 131 and flows into the second part 171-2 of the insertion hole/channel 171 arranged within the inlay cap 170. Via this second part 171-2 of the insertion hole/channel 171 arranged within the inlay cap 170, the liquid flows via the adapter counterpart 175 into further channels (not shown) guiding the liquid into the liquid reservoir (not shown) of an electronic smoking device. The liquid entering the liquid reservoir will push air out of the liquid reservoir which will be guided out of the liquid reservoir via additional channels (not shown). The air pushed out of the liquid reservoir will exit the adapter counterpart 175 of the electronic smoking device and the inlay cap 170 via the airflow channel 172 arranged within the inlay cap 170 and will be released to the surrounding environment via the air release portion 150.

Figure 6:
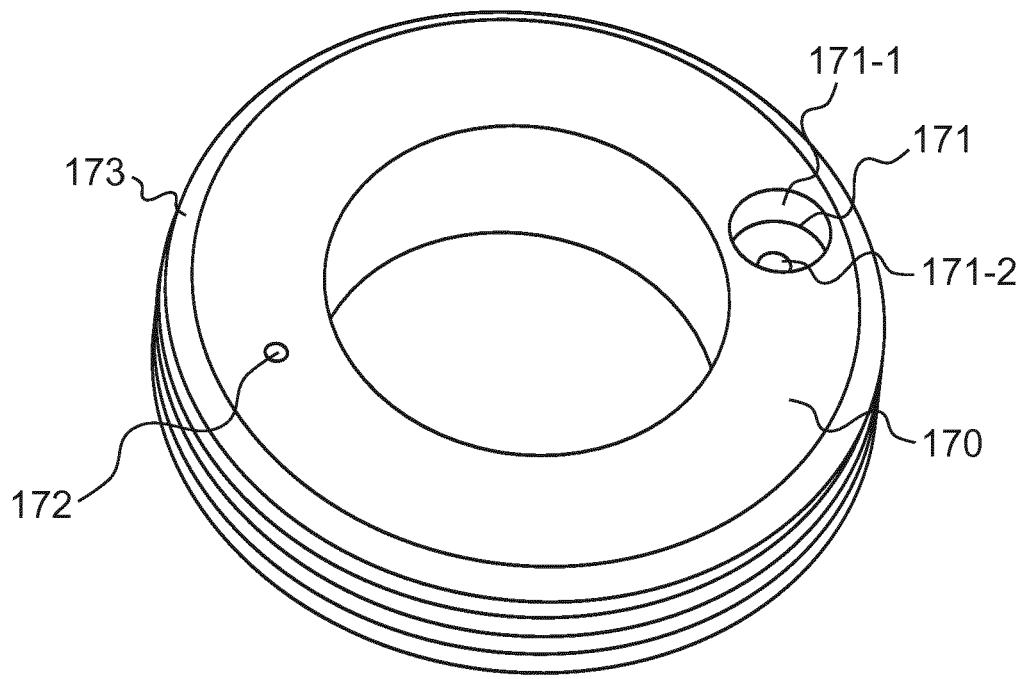
FIG. 6 is a schematic illustration of the inlay cap of the second embodiment of the refill adapter cap.

In FIG. 6, a schematic illustration of the inlay cap 170 of the second embodiment of the refill adapter cap 100 is shown. The inlay cap 170 has the shape of a ring with a flat front surface and a flat rear surface (not shown). Furthermore, the inlay cap 170 comprises an outer screw thread allowing for the inlay cap 170 to be threaded into a corresponding internal thread, for example of an adapter counterpart 175. Moreover, the inlay cap 170 comprises an insertion hole 171 which in this second embodiment is realized within a center of the flat front surface of the inlay cap 170. In this second embodiment, the insertion hole 171 exemplarily resembles a channel that spatially interconnects the flat front surface and the flat rear surface of the inlay cap 170. In this second embodiment, the channel representing the insertion hole 171 exemplarily has two different parts 171-1, 171-2 wherein each of the two parts 171-1, 171-2 has its own diameter. The diameter of the first part 171-1 of the channel in the inlay cap 170 is chosen to be larger than the diameter of the second part 171-2, such that the injection portion 130 of the refill adapter cap 100 (see FIG. 5) can be directly inserted into the first part 171-1 of the insertion hole 171. The second part 171-2 of the insertion hole/channel 171 within the inlay cap 170 has a diameter that is smaller than diameter of the first part 171-1 of the insertion hole/channel 171.

Furthermore, the inlay cap 170 comprises an airflow channel 172 on a side of the inlay cap 170 which is diametrally opposing the side of the inlay cap 170 in which the insertion hole 171 is arranged in. The airflow channel 172 in this embodiment exemplarily has a diameter that is smaller than the diameter of the second part 171-2 of the insertion hole 171. Moreover, in this second embodiment, the outer rim of the flat front surface of the inlay cap 170 exemplarily comprises a chamfered edge 173.

However, also other inlay caps 170 can be realized with other insertion holes 171 and/or with other airflow channels 172 arranged therein and/or without a chamfered edge 173.

Figure 7:
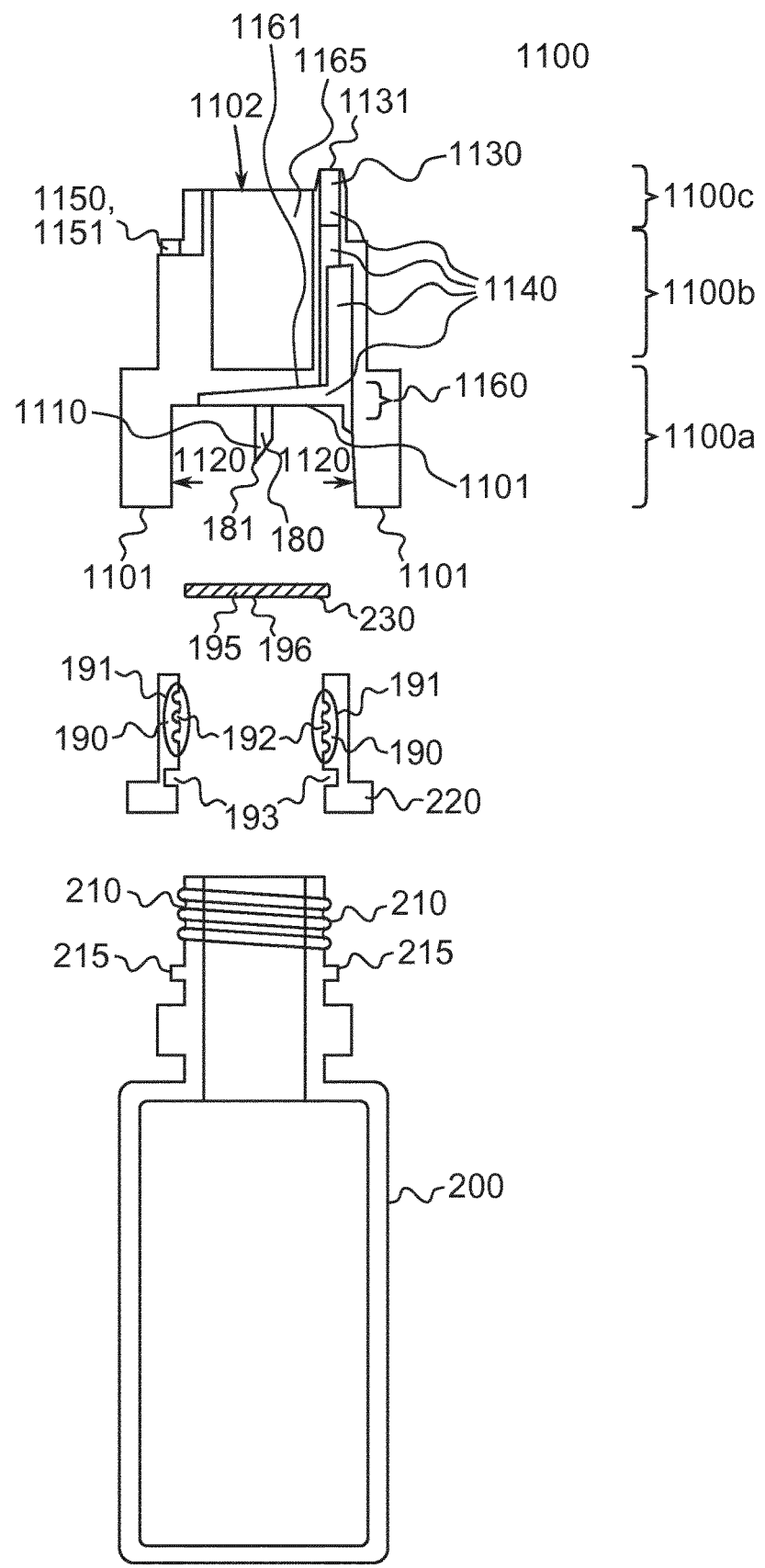
FIG. 7 is a schematic cross-sectional illustration of a third embodiment of a refill adapter cap in an exploded view.

In FIG. 7, a schematic cross-sectional illustration of a third embodiment of a refill adapter cap 1100 in an exploded view is shown. In more detail, FIG. 7 shows a refill adapter cap 1100, an additional collar 190 with a piercing portion 195 which will be described further below and a refill receptacle 200. In this third embodiment, the refill adapter cap 1100 is substantially identical to the refill adapter cap 100 as described hereinbefore. Therefore, also in this third embodiment, the refill adapter cap 1100 comprises three cylindrical, circular portions 1100a, 1100b, 1100c which substantially resemble three cylinders and are equal to the cylindrical, circular portions 100a, 100b, 100c of the first and second embodiment of a refill adapter cap 100 as described hereinbefore. Also in this third embodiment, the refill adapter cap 100 comprises a first end 1101 and a second end 1102 which define the geometrical outlines of the refill adapter cap 1100. Moreover, the refill adapter cap 1100 comprises a connection portion 1120 that in this embodiment is exemplarily realized as a press-fit connection portion. However, also other connection portions 1120 can be realized, comprising other connection elements.

Furthermore, also in this third embodiment, the refill adapter cap 1100 comprises a liquid flow channel 1140 interconnecting the first and the second end 1101, 1102 of the refill adapter cap 1100 so that liquid can flow through the refill adapter cap 1100 and into a liquid reservoir of an electronic smoking device (not shown). Moreover, also in this third embodiment, the liquid flow channel 1140 comprises a slope section 1160 that substantially has the same funnel shape as the slope section 1160 of the first and the second embodiment and also comprises a slanted surface 1161. The liquid flow channel 1140 extends into an injection portion 1130 that protrudes from the second end 1102 of the refill adapter cap 1100 and comprises a liquid outlet hole 1131. The liquid flow channel 1140 is arranged next to a centre hole 1165 which allows for the refill adapter cap 1100 to be centered for example around a protrusion part of an electronic smoking device, adapted for the positioning adjustment of the refill adapter cap 1100.

Moreover, also in this third embodiment, an air release portion 1150 is arranged within the third section 1100c of the refill adapter cap 1100, which in this third embodiment is also realized as a notch 1151.

However, the refill adapter cap 1100 of this third embodiment differs from the embodiments described hereinbefore in that the first end 1101 of the refill adapter cap 1100 comprises a needle 180 with the opening 1110 of the first end 1101 being arranged at the tip 181 of the needle 180, wherein the needle 180 is protruding from the first end 1101, away from the refill adapter cap 1100, along a direction that is parallel to a centerline CL of the refill adapter cap 1100. An advantage of that may be that an undesired spilling of liquid is further prevented as the only opening 1110 of the first end 1101 of the refill adapter cap 1100 is arranged within the tip 181 of the needle 180 which allows to provide the opening 1110 of the refill adapter cap 1100 within a refill receptacle 200 or within a refill bottle. Expressed in other words, the needle 180 can be pierced into a corresponding surface of a refill receptacle 200 or of a refill bottle in order to realize a safe, stable and spill-free connection between the refill adapter cap 1100 and the corresponding refill receptacle 200 or refill bottle. In more detail, in this third embodiment, the liquid can only enter the slope section 1160 of the liquid flow channel 1140 via the opening 1110 that is arranged within the tip 181 of the needle 180. Therefore, the surface of the slope section 1160 that is representing a fraction of the first end 1101 of the refill adapter cap 1100 and that is being arranged perpendicular to the needle 180, is a closed surface of the refill adapter cap 1100. The needle 180 is exemplarily arranged centrally on this closed surface of the refill adapter cap 1100. However, in other embodiments, the needle 180 can also be arranged displaced from the center of this closed surface, for example on a side or rim portion of the surface. Furthermore, in other embodiments, the needle 180 does not represent an actual needle but is an elongated, rod-like component of the refill adapter cap 110 that has a tip with an opening therein and is adapted to pierce a corresponding surface of a refill receptacle 200.

In this third embodiment of the refill adapter cap 1100, the refill adapter cap 1100 further comprises an additional collar 190 that comprises an attachment portion 191 for the separate attachment of the additional collar 190 to a refill receptacle 200 and a piercing portion 195 adapted to be pierced by the needle 180 of the refill adapter cap 1100. An advantage of that may be that the additional collar 190 further seals a refill receptacle 200 as for example a refill bottle when the refill adapter cap 1100 is attached thereto. In this third embodiment, the additional collar 190 is a component of the refill adapter cap 1100 but is however separate therefrom. In other embodiments, the additional collar 190 can also be realized as an outlet collar 220 representing a component of a refill receptacle 200. In such an embodiment, an outlet collar 220 can releasable or non-releasable be put on the refill outlet portion 210 of a refill receptacle 200. Furthermore, such an outlet collar 220 can comprise an own outlet piercing portion 230. However, the additional collar 190 shown in FIG. 7 can separately be attached to a refill receptacle 200. For such an attachment, the additional collar 190 has the shape of a cap and comprises an attachment portion 191 that has an engagement element 192 thereon. Expressed in other words, the attachment portion 191 comprises an engagement element 192 that is adapted to engage with a corresponding engagement element of a refill receptacle 200. An advantage of that may be that the additional collar 190 can easily be connected to a refill receptacle 200 which can for example be realized as a refill bottle. The engagement element 192 can be a releasable or a non-releasable engagement element 192. Such releasable engagement elements 192 exemplarily can be snap-fit connection elements as for example retaining lugs that are adapted to engage with corresponding fixation holes or press-fit elements.

In this third embodiment, the engagement element 192 comprises a screw thread. An advantage of that may be that internal or external screw threads allow for a strong and tight releasable connection between the additional collar 190 and the refill outlet portion 210 of a refill receptacle 200. In this third embodiment, the engagement element 192 is exemplarily realized as an internal screw thread. The internal screw thread allows for the additional collar 190 to be screwed onto a corresponding external screw thread that is arranged on a refill outlet portion 210 of a refill receptacle 200. Moreover, the attachment portion 191 of the additional collar 190 further comprises additional engagement elements 193 which in this third embodiment exemplarily are realized as internal notches which are adapted to engage with corresponding engagement protrusions 215 that are arranged on a refill outlet portion 210 of a refill receptacle 200.

However, it is also possible to realize refill adapter caps 1100 with other engagement elements 192, with other additional engagement elements 193 and/or without additional engagement elements 193. In this third embodiment, the additional collar 190 exemplarily comprises a plastic. However, also other embodiments of refill adapter caps 1100 with other additional collars 190 comprising other materials can be realized.

The additional collar 190 of the refill adapter cap 1100 comprises a piercing portion 195 adapted to be pierced by the needle 180 of the refill adapter cap 1100. In this third embodiment, the piercing portion 195 comprises a membrane 196. An advantage of that may be that a membrane 196 in an intact state on the one hand is capable of safely restoring liquid within a refill receptacle 200 and on the other hand can easily be pierced by the needle 180 of the refill adapter cap 1100. In this third embodiment, the membrane 196 represents the lid of the additional collar 190, so that the membrane 196 seals the opening of a refill outlet portion 210 of a refill receptacle 200 when the additional collar 190 is fully attached to the refill receptacle 200. Expressed in other words, the membrane 196 is arranged such that the additional collar 190 has a U-shape with the membrane 196 interconnecting the two parallel shanks of the U-shape.

The U-shaped additional collar 190 can be put on the refill receptacle 200 with the opening of the U-shaped additional collar 190 that is opposing the membrane 196 enclosing a refill outlet portion 210 of the refill receptacle 200. In this third embodiment, the membrane 196 exemplarily comprises silicone. An advantage of that may be that silicon is a material that easily can be processed and furthermore can easily be pierced by the needle 180 of the refill adapter cap 1100. However, also other embodiments of refill adapter caps 1100 with other additional collars 190 and other membranes 196 comprising other materials can be realized. For example, other membranes 196 can comprise plastics or other elastic materials. Basically, any material suited to serve as a membrane 196 can come to use.

Figure 8:
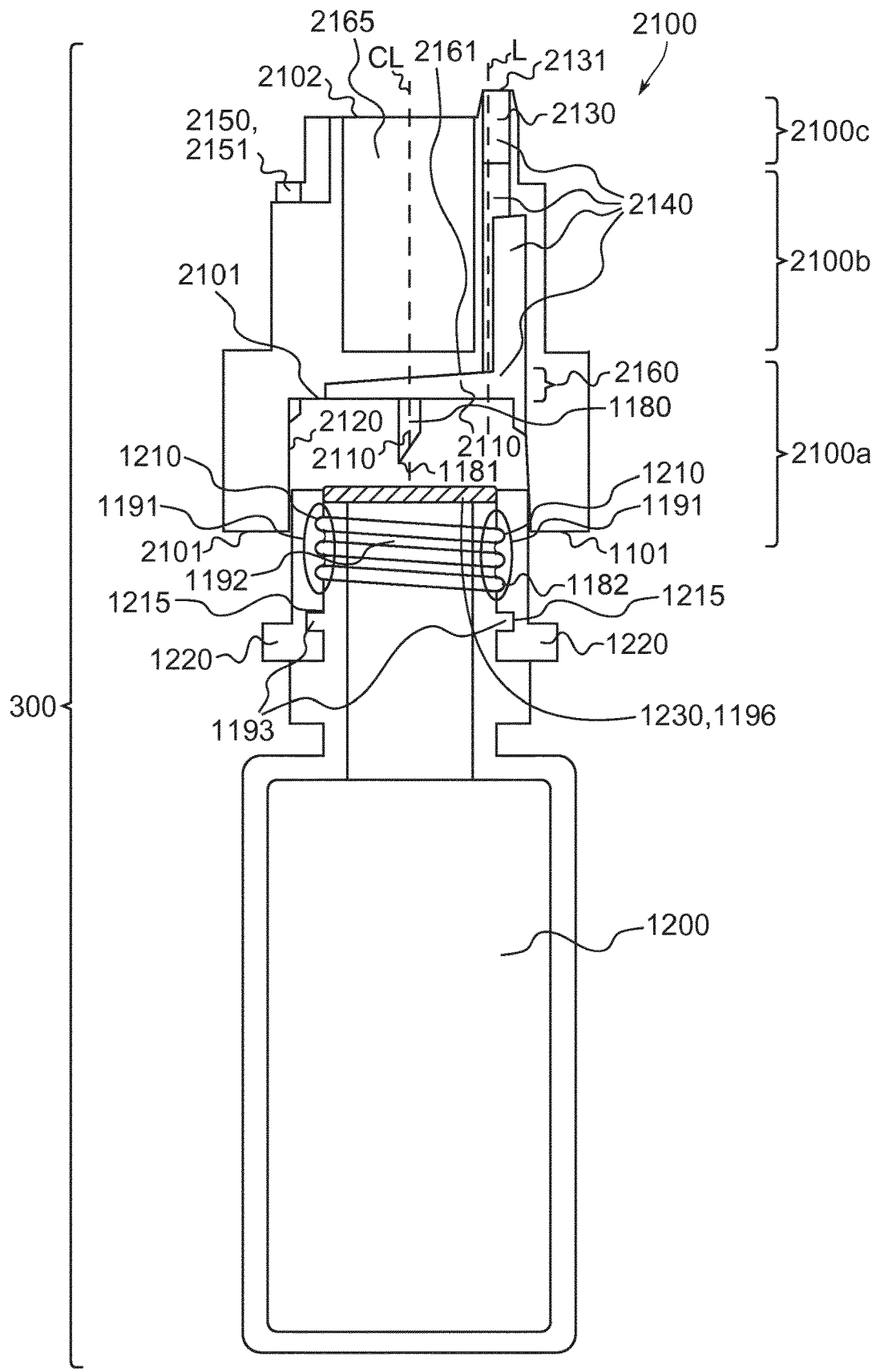
FIG. 8 is a schematic cross-sectional illustration of an embodiment of a refill system in a semi connected state.

In FIG. 8, a schematic cross-sectional illustration of an embodiment of a refill system 300 in a semi connected state is shown. The refill system 300 shown in FIG. 8 is a refill system 300 for an electronic smoking device. The refill system 300 comprises an embodiment of a refill adapter cap 2100 that is substantially identical to the embodiment of the refill adapter cap 1100 described hereinbefore. The refill adapter cap 2100 of this embodiment differs from the third embodiment of the refill adapter cap 1100 in that the refill adapter cap 2100 of the refill system 300 does not comprise an additional collar, which in this embodiment of a refill system 300 is a part of the refill receptacle 1200 described further below. Thus, in this embodiment, the refill adapter cap 2100 also comprises three circular sections 2100a, 2100b, 2100c which also substantially resemble three cylinders and are equal to the cylindrical, circular sections 100a, 100b, 100c of the first, second and third embodiment of a refill adapter cap 100, 1100 as described hereinbefore.

Furthermore, the refill adapter cap 2100 comprises a first end 2101 and a second end 2102 defining the geometrical outlines of the refill adapter cap 2100 shown in FIG. 8. The refill adapter cap 2100 comprises a connection portion 2120 that in this embodiment is exemplarily realized as a press-fit connection portion. Thus, the first of the circular sections 2100a of the refill adapter cap 2100 has a blind hole arranged therein, the blind hole having a diameter that corresponds to the diameter of a counterpart of the refill receptacle 1200, thereby forming a connection portion 2120 of the refill adapter cap 2100 shown in FIG. 8. However, also other connection portions 2120 can be realized, comprising connection elements other than a press-fit connection element.

Furthermore, also in this embodiment, the refill adapter cap 2100 comprises a liquid flow channel 2140 interconnecting the first and the second end 2101, 2102 of the refill adapter cap 2100 so that liquid can flow through the refill adapter cap 2100. Moreover, the liquid flow channel 2140 comprises a slope section 2160 that substantially has the same funnel shape as the slope section 2160 of the third embodiment. Thus, also in this embodiment, the slope section 2160 comprises a slanted surface 2161 allowing for liquid entering the refill adapter cap 2100 to flow into the liquid flow channel 2140 that extends along a line L that is displaced in parallel with respect to a centerline CL of the refill adapter cap 2100. The liquid flow channel 2140 extends into an injection portion 2130 that protrudes from the second end 2102 of the refill adapter cap 2100 and comprises a liquid outlet hole 2131. The liquid flow channel 2140 is arranged next to a center hole 2165 which allows for the refill adapter cap 2100 to be centered for example around a protrusion part of an electronic smoking device. Such a protrusion part of an electronic smoking device can for example be adapted for the positioning adjustment of the refill adapter cap 2100. An air release portion 2150 is arranged within the third section 2100c of the refill adapter cap 2100, which in this embodiment is also realized as a notch 2151.

Also in this embodiment, the refill adapter cap 2100 comprises a needle 1180 with the opening 2110 of the first end 2101 being arranged at the tip 1181 of the needle 1180. The needle 1180 is protruding from the first end 2101, away from the refill adapter cap 2100, along a direction that is parallel to a centerline CL of the refill adapter cap 2100. Liquid can only enter the slope section 2160 of the liquid flow channel 2140 via the opening 2110 that is arranged within the tip 1181 of the needle 1180. Therefore, the surface of the slope section 2160 that is facing the first end 2101 of the refill adapter cap 2100 and that is being arranged perpendicular to the needle 1180, is a closed surface of the refill adapter cap 2100. The needle 1180 is exemplarily arranged centrally on this closed surface of the refill adapter cap 2100. However, in other embodiments, the needle 1180 can also be arranged displaced from the center of this closed surface, for example on a side or rim portion of the surface.

Furthermore, the refill system 300 comprises a refill receptacle 1200 with a refill outlet portion 1210 and an outlet collar 1220 attached to the refill outlet portion 1210, wherein the outlet collar 1220 comprises an outlet piercing portion 1230 adapted to be pierced by the needle 1180 of the refill adapter cap 2100. An advantage of that may be that such a refill system 300 allows for a handy and spill-safe refill of the liquid reservoir of an electronic smoking device.

In this embodiment, the refill receptacle 1200 is a refill bottle that comprises a refill outlet portion 1210 which comprises a bottle head with an opening for the release of liquid contained within the liquid body. The outlet collar 1220 of the refill system 300 is substantially identical to the additional collar 190 that was described hereinbefore with respect to FIG. 7. In this embodiment, the outlet collar 1220 is a component of the refill adapter cap 1100 but is however separate therefrom. Thus, the outlet collar 1220 can separately be attached to a refill receptacle 1200. In more detail, the outlet collar 1220 has the shape of a bottle cap and comprises an attachment portion 1191 that has an engagement element 1192 thereon. Expressed in other words, the attachment portion 1191 comprises an engagement element 1192 that is adapted to engage with a corresponding engagement element of a refill receptacle 1200. In this embodiment, the engagement element 1192 is also realized as an internal thread that is shown in a state in which it is engaged with the external thread of the refill outlet portion 1210 of the refill receptacle 1200.

In principal, the engagement element 1192 can be a releasable or a non-releasable engagement element 1192. Besides screw-fit connection elements, a releasable engagement element 1192 exemplarily can comprise a snap-fit connection element comprising for example retaining lugs that are adapted to engage with corresponding fixation holes or press-fit connection elements. Moreover, the attachment portion 1191 of the outlet collar 1220 further comprises additional engagement elements 1193 which in this embodiment exemplarily are realized as internal notches which are adapted to engage with corresponding engagement protrusions 1215 that are arranged on the refill outlet portion 1210 of the refill receptacle 1200.

However, it is also possible to realize other refill systems 300 with other outlet collars 1220 that comprise other engagement elements 1192, with other additional engagement elements 1193 and/or without additional engagement elements 1193. In this embodiment, the additional collar 1190 exemplarily comprises a plastic. However, also other embodiments of refill systems 300 with other outlet collars 1220 comprising other materials can be realized.

The outlet collar 1220 of the refill system 300 comprises an outlet piercing portion 1230 adapted to be pierced by the needle 1180 of the refill adapter cap 2100. In this embodiment, the outlet piercing portion 1230 comprises a membrane 1196 which represents the lid of the outlet collar 1220, so that the membrane 1196 seals the opening of a refill outlet portion 1210 of the refill receptacle 1200 when the outlet collar 1220 is fully attached to the refill receptacle 1200 as it is shown in FIG. 8. Expressed in other words, the membrane 1196 is arranged such that the outlet collar 1220 has a U-shape with the membrane 1196 interconnecting the two parallel shanks of the U-shape.

As shown in FIG. 8, the U-shaped outlet collar 1220 is put on the refill receptacle 1200 with the opening of the U-shaped outlet collar 1220 opposing the membrane 1196 enclosing the head of the bottle shaped refill receptacle 200. In this embodiment, the membrane 1196 exemplarily comprises a foil. However, also other embodiments of refill systems 300 with other outlet collars 1220 and other membranes 1196 comprising other materials can be realized. For example, other membranes 1196 can comprise silicone, plastics or other elastic materials. Basically, any material suited to serve as a membrane 1196 can come to use.

In FIG. 8, the refill adapter cap 2100 is not fully connected to the refill bottle. In the semi connected state shown in FIG. 8, the needle 1180 of the refill adapter cap 2100 has not pierced through the outlet piercing portion 1230, so the membrane 1196 of the outlet collar 1220 is still intact.

Figure 9:
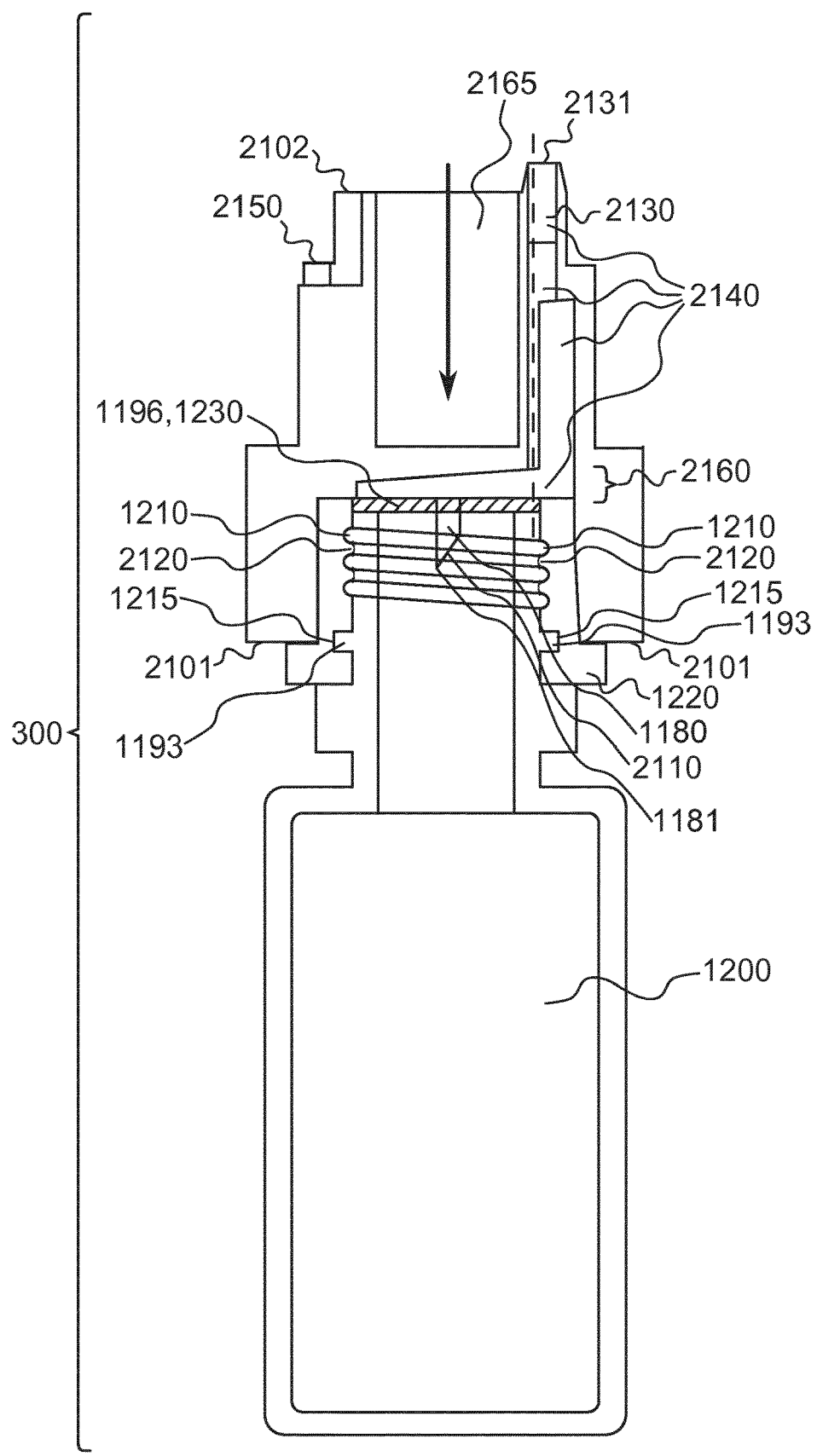
FIG. 9 is a schematic cross-sectional illustration of the embodiment of the refill system in a fully connected state.

In FIG. 9, it is shown a schematic cross-sectional illustration of the embodiment of the refill system 300 in a fully connected state. In this connected state, the refill adapter cap 2100 of the refill system 300 is fully connected to the refill bottle, so the refill adapter cap 2100 has been pushed onto the outlet collar 1220 which is arranged on the refill outlet portion 1210 of the refill bottle. In FIG. 9, an arrow indicates the direction in which the refill adapter cap 2100 has been pushed. Therefore, the needle 1180 of the refill adapter cap 2100 has fully pierced the outlet piercing portion 1230, so the membrane 1196 of the outlet collar 1220. The surface of the slope section 1260 is in contact with the membrane 1196 of the outlet collar 1220 and the connection portion 2120 of the refill adapter cap 2100 is press-fit connected to the outlet collar 1220. In this state, the opening 2110 of the first end 2101 of the refill adapter cap 2100, which is arranged within the tip 1181 of the needle 1180, is provided within the refill receptacle 1200 of the refill system 300.

In the fully connected state of the refill system 300 shown in FIG. 9, the refill system 300 is ready to be used in order to refill the liquid reservoir of an electronic smoking device. Therefore, the injection portion 2130 with the liquid outlet hole 2131 is inserted into a corresponding insertion hole of an electronic smoking device or of an inlay cap 170 as for example shown in FIG. 6. When the refill system 300 is brought to an upright position with the refill bottle being arranged above the refill cap 2100 relative to the ground, liquid will flow from the refill bottle into the opening 2110 arranged within the tip 1181 of the needle 1180. From there, the liquid will flow down the needle 1180 and enter the slope section 1160 of the refill adapter cap 2100. From the slope section 1160, the liquid flows down the liquid flow channel 2140 and into the injection portion 2130. The liquid will then exit the refill adapter cap 2100 via the liquid outlet hole 2131 and enter the electronic smoking device or a further component as an inlay cap 170 as mentioned further above.

A refill adapter cap for a refill receptacle is presented, wherein the refill receptacle is adapted to refill the liquid reservoir of an electronic smoking device via the refill adapter cap, wherein the refill adapter cap comprises a first end with an opening and a connection portion, adapted for the connection to a refill receptacle. Furthermore, the refill adapter cap comprises a second end with an injection portion that protrudes from the second end and comprises a liquid outlet hole. Moreover, the refill adapter cap comprises a liquid flow channel interconnecting the first end and the second end, allowing for liquid to flow through the refill adapter cap. The liquid flow channel comprises a slope section adapted to reduce the flow rate of liquid passing the liquid flow channel. The slope section extends from the first end along a part of the liquid flow channel and has a tapering cross-section.

An advantage of that may be that such a refill adapter cap allows for a safe and stable connection between a refill receptacle adapted for the refilling of the liquid reservoir of an electronic smoking device and an opening of the electronic smoking device itself. Furthermore, via such a refill adapter cap, spilling of e-liquid or liquid adapted to be vaporized is avoided.

Preferably, the slope section of the liquid flow channel at the first end has a diameter that is at least as great as the diameter of the opening. In such an embodiment, liquid can enter the slope section quickly but is slowed down from the opening of the slope section on. This allows for an efficient reduction of the flow rate of liquid flowing within the refill adapter cap which further reduces spilling of liquid passing the refill adapter cap.

In a preferred embodiment, the liquid flow channel at least in part extends along a line that is displaced in parallel with respect to a centerline of the refill adapter cap. In such an embodiment, a center portion of the refill adapter cap can be used to adjust the position of the refill adapter cap in relation to an electronic smoking device. Preferably, the center portion of the refill adapter cap comprises a center hole corresponding to a protrusion arranged on or in an electronic smoking device, adapted to adjust the position of the refill adapter cap.

In a preferred embodiment, the slope section of the liquid flow channel has the shape of a funnel. In such an embodiment, the slope section efficiently allows for a decrease of the flow rate of the liquid flowing within the refill adapter cap.

Preferably, the connection portion comprises a screw fit connection element. Such a screw fit connection element allows for an easy but nevertheless stable connection of the refill adapter cap and a refill receptacle. Furthermore preferred, the connection portion comprises a snap-fit connection element and/or a push-fit connection element.

In a preferred embodiment, the refill adapter cap further comprises an inlay cap adapted to be arranged within an opening of an electronic smoking device, wherein the inlay cap comprises an insertion hole for the reception of the injection portion of the refill adapter cap, allowing for liquid to flow through the inlay cap. In such an embodiment, the inlay cap can be used as a further adapter allowing for an improved transfer of liquid from a refill receptacle to the liquid reservoir of an electronic smoking device. Furthermore, such an inlay cap can be chosen depending on the electronic smoking device that is to be refilled, so that different shapes of inlay caps correspond to different sorts of electronic smoking devices or liquid reservoirs.

Preferably, the inlay cap further comprises an airflow channel allowing for air to flow through the inlay cap. In such an embodiment, a pressure equalization of the liquid reservoir is guaranteed during a refill process of the liquid reservoir of an electronic smoking device. Preferably, the airflow channel of the inlay cap and the air release portion of the refill adapter cap are aligned when the injection portion of the refill adapter cap is inserted into the insertion hole of the inlay cap.

Preferably, the inlay cap comprises a connection element adapted to connect the inlay portion to a component of an electronic smoking device. Preferably, the connection of the inlay cap is realized as an outer screw thread or an inner screw thread.

Preferably, the inlay cap has the shape of a ring or of a hollow cylinder.

In a preferred embodiment, the first end comprises a needle with the opening of the first end being arranged at the tip of the needle, wherein the needle is protruding from the first end, away from the refill adapter cap, along a direction that is parallel to a centerline of the refill adapter cap. In such an embodiment, spilling of liquid during a refill process using a refill adapter cap that is connected to a refill receptacle is efficiently avoided, since the opening of the refill adapter cap is provided directly within a refill receptacle or within a refill bottle.

Preferably, the refill adapter cap further comprises an additional collar that comprises an attachment portion for the separate attachment of the additional collar to a refill receptacle and/or a piercing portion adapted to be pierced by the needle of the refill adapter cap. In such an embodiment, spilling of liquid is further avoided as the piercing portion additionally holds back liquid within the refill receptacle or a refill bottle during a refill process. Furthermore, the additional collar allows for an improved and stronger connection between the refill adapter cap and the refill receptacle.

In a preferred embodiment, the attachment portion comprises an engagement element adapted to engage with a corresponding engagement element of a refill receptacle. Such an engagement element allows for an improved and stable releasable or non-releasable connection of the additional collar and the refill receptacle. Preferably, the engagement element is a screw-fit connection element, a friction push-fit connection element, a snap-fit connection element, a bayonet connection element and/or a magnetic fit connection element.

Preferably, the engagement element comprises a screw thread. Screw threads are easy to realize and allow for an easily releasable connection between two components.

In an even more preferred embodiment, the piercing portion comprises a membrane. A membrane can easily be pierced by a needle but nevertheless allows to efficiently retain liquid within a refill receptacle.

Preferably, the membrane comprises silicone. Silicone is a cost-efficient material and a to a high degree impermeable material that can easily be processed.

Furthermore, a refill system for an electronic smoking device is provided. The refill system comprises a refill adapter cap and a refill receptacle with a refill outlet portion and an outlet collar attached to the refill outlet portion, wherein the outlet collar comprises an outlet piercing portion adapted to be pierced by the needle of the refill adapter cap. Such a refill system allows for a safe, efficient and especially dry refill of an electronic smoking device. Expressed in other words, such a refill system allows for an electronic smoking device to be refilled with e-liquid without that liquid is spilled avoiding inconvenient events for the user when refilling an electronic smoking device.

While this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims.

LIST OF REFERENCE SIGNS 10 electronic smoking device
12 power supply portion
14 atomizer/liquid reservoir portion
16 end cap
18 battery
20 light-emitting diode (LED)
22 control electronics
24 airflow sensor
26 atomizer
28 heating coil
30 wick
32 central passage
34 liquid reservoir
36 air inhalation port
38 air inlets
100, 1100, 2100 refill adapter cap
100a, 1100a, 2100a first circular section
100b, 1100b, 2100b second circular section
100c, 1100c, 2100c third circular section
101, 1101, 2101 first end
102, 1102, 2102 second end
110, 1110, 2110 opening
120, 1120, 2120 connection portion
130, 1130, 2130 injection portion
131, 1131, 2131 liquid outlet hole
140, 1140, 2140 liquid flow channel
150, 1150, 2150 air release portion
151, 1151, 2151 notch
160, 1160, 2160 slope section
160-1 accumulative portion
160-2 discharge portion
161, 1161, 2161 slanted surface
165, 1165, 2165 center hole
170 inlay cap
171 insertion hole
171-1 first part of the insertion hole/channel
171-2 second part of the insertion hole/channel
172 airflow channel
173 chamfered edge
175 adapter counterpart
180, 1180 needle
181, 1181 tip
190 additional collar
191, 1191 attachment portion
192, 1192 engagement element
193, 1193 additional engagement element
195 piercing portion
196, 1196 membrane
200, 1200 refill receptacle
210, 1210 refill outlet portion
215 engagement protrusions
220, 1220 outlet collar
230, 1230 outlet piercing portion
300 refill system
L line
CL centerline

The invention claimed is:

1. A refill adapter cap for a refill receptacle adapted to refill a liquid reservoir of an electronic smoking device via the refill adapter cap, wherein the refill adapter cap comprises:
   a first end with an opening and a connection portion, adapted for the connection to a refill receptacle;
   a second end with an injection portion that protrudes from an edge end surface of second end and comprises a liquid outlet hole;
   a liquid flow channel interconnecting the first end and the second end, allowing for liquid to flow through the refill adapter cap;
   wherein the liquid flow channel comprises a slope section adapted to reduce the flow rate of liquid passing the liquid flow channel.

2. The refill adapter cap of claim 1, wherein the slope section extends from the first end along a part of the liquid flow channel and has a tapering cross-section.

3. The refill adapter cap of claim 2, wherein the slope section of the liquid flow channel at the first end has a diameter that is at least as great as the diameter of the opening.

4. The refill adapter cap of claim 1, wherein the liquid flow channel at least in part extends along a line that is displaced in parallel with respect to a centerline of the refill adapter cap.

5. The refill adapter cap of claim 1, wherein the slope section of the liquid flow channel includes the shape of a funnel.

6. The refill adapter cap of claim 1, wherein the connection portion comprises a screw-fit connection element.

7. The refill adapter cap of claim 1, further comprising an inlay cap adapted to be arranged within an opening of an electronic smoking device, wherein the inlay cap comprises an insertion hole for the reception of the injection portion of the refill adapter cap, allowing for liquid to flow through the inlay cap.

8. The refill adapter cap of claim 7, wherein the inlay cap further comprises an airflow channel allowing for air to flow through the inlay cap.

9. The refill adapter cap of claim 1, wherein the first end comprises a needle with the opening of the first end being arranged at the tip of the needle, wherein the needle is protruding from the first end, away from the refill adapter cap, along a direction that is parallel to a centerline of the refill adapter cap.

10. The refill adapter cap of claim 9, further comprising an additional collar that comprises an attachment portion for the separate attachment of the additional collar to a refill receptacle or a piercing portion adapted to be pierced by the needle of the refill adapter cap.

11. The refill adapter cap of claim 10, wherein the attachment portion comprises an engagement element adapted to engage with a corresponding engagement element of a refill receptacle.

12. The refill adapter cap of claim 11, wherein the engagement element comprises a screw thread.

13. The refill adapter cap of claim 10, wherein the piercing portion comprises a membrane.

14. The refill adapter cap of claim 13, wherein the membrane comprises silicone.

15. The refill adapter cap of claim 1, wherein the liquid flow channel at least in part extends along a line that is displaced in parallel with respect to a centerline of the refill adapter cap.

16. A refill system for an electronic smoking device, comprising:
 a refill adapter cap for a refill receptacle adapted to refill a liquid reservoir of an electronic smoking device via the refill adapter cap, wherein the refill adapter cap comprises:
  a first end with an opening and a connection portion, adapted for the connection to a refill receptacle;
  a second end with an injection portion that protrudes from an edge end surface of second end and comprises a liquid outlet hole;
  a liquid flow channel interconnecting the first end and the second end, allowing for liquid to flow through the refill adapter cap, wherein the liquid flow channel comprises a slope section adapted to reduce the flow rate of liquid passing the liquid flow channel;
  a needle at the first end, wherein the opening of the first end being arranged at the tip of the needle, and wherein the needle is protruding from the first end, away from the refill adapter cap, along a direction that is parallel to a centerline of the refill adapter cap; and
 a refill receptacle with a refill outlet portion and an outlet collar attached to the refill outlet portion, wherein the outlet collar comprises an outlet piercing portion adapted to be pierced by the needle of the refill adapter cap.

17. The refill adapter cap of claim 16, wherein the slope section extends from the first end along a part of the liquid flow channel and has a tapering cross-section.

18. The refill adapter cap of claim 16, further comprising an additional collar that comprises an attachment portion for the separate attachment of the additional collar to a refill receptacle or a piercing portion adapted to be pierced by the needle of the refill adapter cap.

19. The refill adapter cap of claim 18, wherein the piercing portion comprises a membrane.

20. The refill adapter cap of claim 18, wherein the attachment portion comprises an engagement element adapted to engage with a corresponding engagement element of a refill receptacle.

* * * * *